US008491840B2

(12) United States Patent
Cho et al.

(10) Patent No.: US 8,491,840 B2
(45) Date of Patent: Jul. 23, 2013

(54) MICROFLUIDIC DEVICE, SAMPLE ANALYZING METHOD USING THE SAME, AND DILUTION RATIO MEASURING METHOD

(75) Inventors: Yoon-kyoung Cho, Suwon-si (KR); Yang-ui Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 485 days.

(21) Appl. No.: 12/501,681

(22) Filed: Jul. 13, 2009

(65) Prior Publication Data

US 2010/0009457 A1 Jan. 14, 2010

(30) Foreign Application Priority Data

Jul. 14, 2008 (KR) ........................ 10-2008-0068343

(51) Int. Cl.
*B01L 3/00* (2006.01)
*G01N 33/50* (2006.01)

(52) U.S. Cl.
USPC ........... 422/68.1; 422/502; 422/503; 422/506

(58) Field of Classification Search
None
See application file for complete search history.

(56) References Cited

U.S. PATENT DOCUMENTS

| | | | | |
|---|---|---|---|---|
| 6,063,589 | A * | 5/2000 | Kellogg et al. | 435/24 |
| 2008/0193336 | A1 * | 8/2008 | Cho et al. | 422/100 |
| 2009/0238724 | A1 * | 9/2009 | Yamamoto et al. | 422/68.1 |

FOREIGN PATENT DOCUMENTS

WO WO 2007052648 A1 * 5/2007

* cited by examiner

*Primary Examiner* — Yelena G Gakh
*Assistant Examiner* — Christopher A Hixson
(74) *Attorney, Agent, or Firm* — Sughrue Mion, PLLC

(57) ABSTRACT

Provided are a microfluidic device, a method of analyzing a sample using the microfluidic device, and a method of measuring dilution ratios. The microfluidic device includes: a sample chamber which accommodates a sample to be tested; a dilution chamber which accommodates a diluent, receives the sample from the sample chamber, and provides a sample diluent; a first concentration detecting chamber which receives the sample from the sample chamber; and a second concentration detecting chamber which receives the sample diluent from the dilution chamber.

12 Claims, 3 Drawing Sheets

MICROFLUIDIC DEVICE, SAMPLE ANALYZING METHOD USING THE SAME, AND DILUTION RATIO MEASURING METHOD

CROSS-REFERENCE TO RELATED APPLICATIONS

This application claims priority from Korean Patent Application No. 10-2008-0068343, filed on Jul. 14, 2008 in the Korean Intellectual Property Office, the disclosure of which is incorporated herein in its entirety by reference.

BACKGROUND

1. Field

One or more exemplary embodiments of the inventive concept relate to a microfluidic device comprising a microfluidic structure, a method of analyzing samples using the microfluidic device, and a method of measuring dilution ratios.

2. Description of the Related Art

Various methods of analyzing samples have been developed to, for example, monitor environments, examine food, or diagnose the medical condition of a patient. However, these methods require many manual operations and various devices. To perform an examination according to a predetermined protocol, those skilled in the manual operations repeatedly perform various processes including loading of a reagent, mixing, isolating and transporting, reacting, and centrifuging. However, such repeated manual processes may produce erroneous results due to "human error."

To perform examinations quickly, skilled clinical pathologists are needed. However, it can be difficult for even a skilled clinical pathologist to perform various examinations at the same time. Even more serious, rapid examination results are necessary for immediate treatment of emergency patients. Accordingly, there is a need to develop various types of equipment enabling the simultaneous, rapid and accurate performing of pathological examinations for given circumstances.

Conventional pathological examinations are performed with large and expensive pieces of automated equipment and a relatively large amount of a sample, such as blood. Moreover, results of pathological examinations are only available from two days (at a minimum) to roughly two weeks after receiving the blood sample from a patient.

In order to address the above described problems, small and automated pieces of equipment for analyzing a sample taken from one or, if necessary, a small number of patients over a short time period have been developed. An example of such a system involves the use of a microfluidic device as follows. Initially, blood is loaded into a disc-shaped microfluidic device and the disc-shaped microfluidic device is rotated so that serum is be isolated from blood due to the centrifugal force. The isolated serum is mixed with a predetermined amount of a diluent and the mixture then flows into a plurality of reaction chambers in the disc-shaped microfluidic device. Next, the reaction chambers are filled with reagents prior to allowing the mixture to flow therein. The reagents used may differ according to of the goal of the blood tests. When the serum reacts with different reagents, predetermined colors may appear. The change in color is used to perform blood analysis.

In this type of analyzing device, the dilution ratio of the sample and the diluent greatly affect the reliability of the test.

SUMMARY

One or more exemplary embodiments provide a microfluidic device capable of automatically performing blood biochemical tests for various test items.

One or more exemplary embodiments also provide a microfluidic device capable of providing samples by diluting the samples according to various ratios.

In addition, one or more exemplary embodiments provide a microfluidic device capable of detecting dilution ratios of sample diluents, a sample analysis method, and a method of detecting the dilution ratios.

Additional aspects and/or advantages will be set forth in part in the description which follows and, in part, will be apparent from the description, or may be learned by practice of the invention.

According to an aspect of one or more exemplary embodiments, there is provided a microfluidic device including: a sample chamber; a dilution chamber accommodating a diluent, receiving samples needed for a test from the sample chamber, and providing a sample diluent; a first concentration detecting chamber receiving the samples from the sample chamber; and a second concentration detecting chamber receiving the sample diluent from the dilution chamber.

The microfluidic device may further include a plurality of reaction chambers respectively accommodating a reagent, and receiving the sample diluent from the dilution chamber.

The microfluidic device may have a rotating disk form.

The microfluidic device may include a sample separator separating the sample supplied from the sample chamber, wherein a supernatant of the separated sample is supplied to the dilution chamber and the first concentration detecting chamber.

The microfluidic device may further include a measuring chamber accommodating a fixed amount of the supernatant and being disposed between the sample separator and the dilution chamber.

The microfluidic device may further include an excess sample storing unit that is connected to the sample separator and storing an excess amount of the sample.

The first and second concentration detecting chambers may be positioned at a same distance from a rotation center of the microfluidic device.

Distances from a rotation center of the microfluidic device to the first and second concentration detecting chambers may be with the same as distances from the rotation center of the microfluidic device to the plurality of reaction chambers.

The microfluidic device may include a plurality of the first concentration detecting chambers.

The microfluidic device may include a plurality of the second concentration detecting chambers.

The microfluidic device may include a plurality of dilution chambers providing a plurality of sample diluents having different dilution ratios.

According to another aspect of one or more exemplary embodiments, there is provided a method of analyzing samples, the method including: loading a sample diluent at a predetermined ratio into a plurality of reaction chambers respectively accommodating a reagent and analyzing a sample; and detecting the dilution ratio of the sample diluent and checking the reliability of the sample analysis.

The concentration of the sample may not be fixed.

The checking of the reliability may include: loading the sample and the sample diluent into the first and second concentration detecting chambers, respectively; detecting light absorption values of the sample and the sample diluent accommodated in the first and second concentration detecting chambers; estimating a light absorption value of the sample diluent from the light absorption value of the sample, the dilution ratio of the sample diluent, and the depth of the first and second concentration chambers; and comparing the estimated light absorption value and the detected light absorption value of the sample diluent.

According to another aspect of one or more exemplary embodiments, there is provided a method of measuring dilution ratios comprising: loading a sample and a sample diluent into first and second concentration detecting chambers; detecting light absorption values of the sample and the sample diluent, respectively, that are accommodated in the first and second concentration detecting chambers; and calculating a dilution ratio of the sample diluent based on the light absorption ratio of the sample, the depth of the first and second concentration chambers, and the light absorption value of the sample diluent.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION OF THE EXEMPLARY EMBODIMENTS

Figure 1:
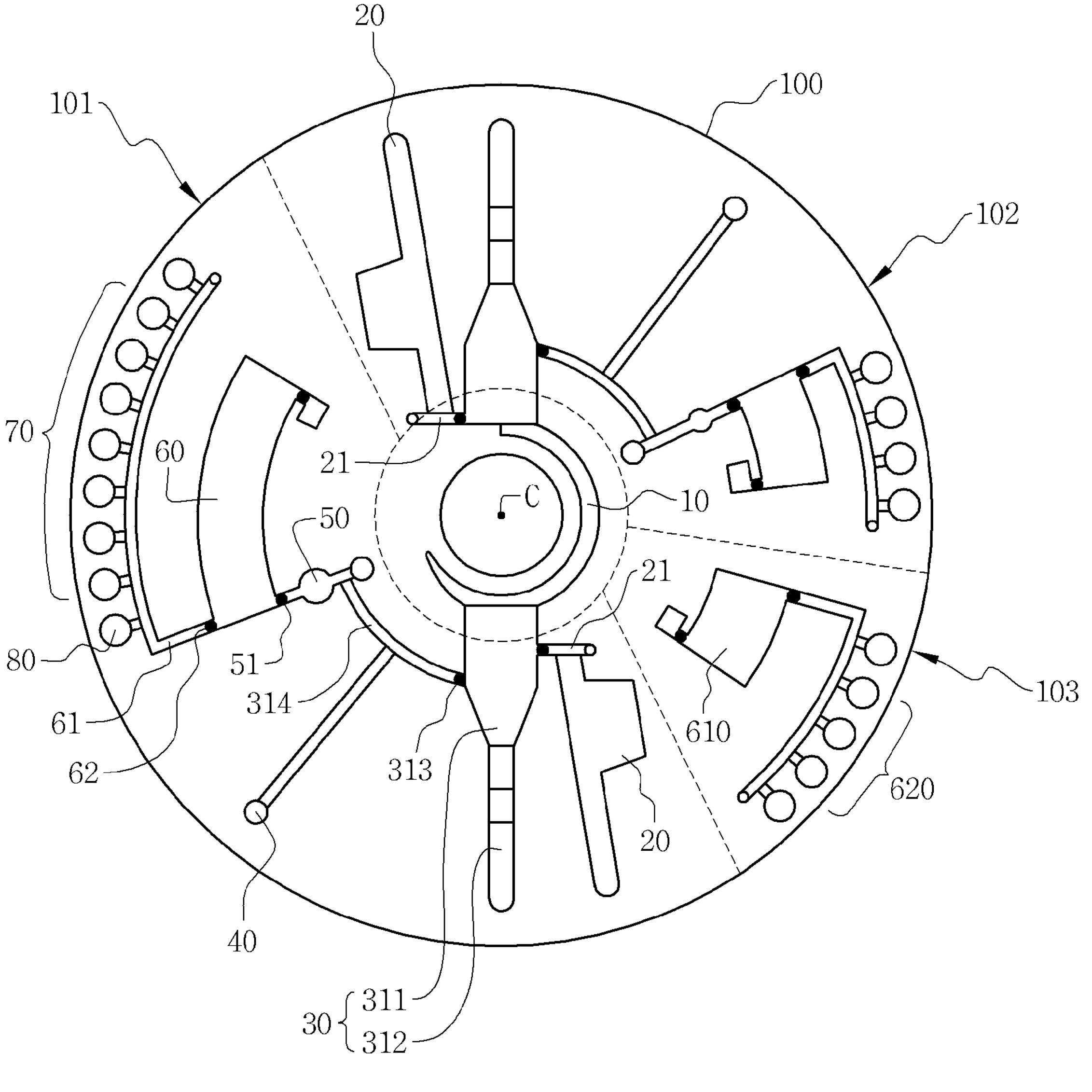
FIG. 1 illustrates a microfluidic device according to an exemplary embodiment.

Reference will now be made in detail to exemplary embodiments, examples of which are illustrated in the accompanying drawings, wherein like reference numerals refer to the like elements throughout. In this regard, the present invention may be embodied in many different forms and should not be construed as being limited to the exemplary embodiments set forth herein. Accordingly, exemplary embodiments are merely described below, by referring to the figures, to explain aspects of the present invention.

FIG. 1 illustrates a microfluidic device according to an exemplary embodiment. The microfluidic device includes a rotatable platform 100, for example, a disk-shaped platform, and microfluidic structures that provide space to accommodate fluid or channels through which the fluid can flow in the platform 100. The platform 100 is rotatable around a center C. That is, the microfluidic device can be mounted on and rotated by a rotation driving unit 510 of an analyzer (see FIG. 4). In this case, in the microfluidic structures arranged in the platform 100, samples can be moved, centrifuged, mixed, and so forth according to the centrifugal operation due to the rotation of the platform 100.

Figure 2:
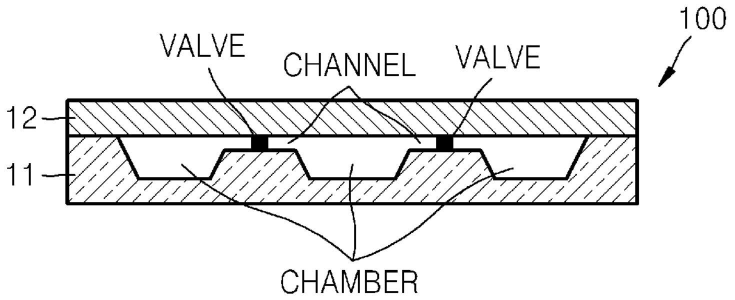
FIG. 2 is a cross-sectional view of a two-layered microfluidic device according to an exemplary embodiment.
Figure 3:
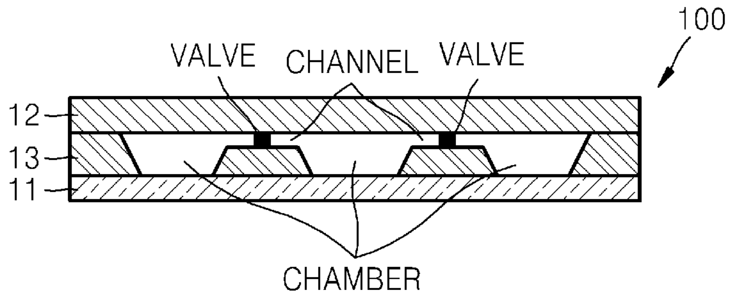
FIG. 3 is a cross-sectional view of a three-layered microfluidic device according to an exemplary embodiment.

The platform 100 may be formed of a plastic material such as acryl, polydimethylsiloxane (PDMS), etc. which can be easily molded and has a biologically inactive surface. However, the material of the platform 100 is not limited thereto, and may be any material that has biological stability, optical transparency, and mechanical processibility. The platform 100 may be formed of various layers. Depressed structures like a chamber or channel are formed in a surface where layers meet each other, and by bonding the layers, space and channels can be provided inside the platform 100. The layers are bonded using an adhesive or a double-sided adhesive tape, or by ultrasonic fusion, laser welding, etc. For example, as illustrated in FIG. 2, the platform 100 may be a two-layered structure including a lower layer 11 and an upper layer 12. Also, as illustrated in FIG. 3, the platform 100 may be a structure including a partition plate 13 for defining a space for accommodating a fluid and a flow channel through which the fluid can flow. The platform 100 may also be formed in various other ways.

The microfluidic structures arranged in the platform 100 will be described hereafter. Portions disposed radially further away from the center C of the platform 100 are referred to as 'exterior'. A sample chamber 10 is disposed radially closer to the center C of the platform 100 than the other microfluidic structures of the microfluidic device. The sample chamber 10 accommodates a predetermined amount of a sample, for example, blood. Although not specifically illustrated in FIG. 1, the sample can be loaded through a sample loading opening which is connected to the sample chamber 10.

For example, the microfluidic device according to the current exemplary embodiment includes two testing units 101 and 102 which are connected to the sample chamber 10. For example, test items such as ALB (Albumin), ALP (Alanine Phosphatase), AMY (Amylase), BUN (Urea Nitrogen), Ca++ (calcium), CHOL(Total Cholesterol), Cl— (Chloide), CRE (Creatinine), GLU (Glucose), HDL (High-Concentration Lipoprotein cholesterol), K+ (Potassium), LD (Lactate Dehydrogenase), Na+ (Sodium), T-BIL (Total Bilirubin), TP (Total Protein), TRIG (Triglycerides), and UA (Uric Acid) require a 1:100 dilution ratio of serum to diluent. Also, ALT (alanine aminotransferase), AST (aspartate aminotransferase), CK (Creatin Kinase), D-BIL (Direct Bilirubin), and GGT (Gamma Glutamyl Transferase) require a 1:20 dilution ratio of serum to diluent. Accordingly, the testing unit 101 may be for testing test items that require a 1:100 dilution ratio of serum to diluent, and the testing unit 102 may be for testing test items that require a 1:20 dilution ratio of serum to diluent.

The two testing units 101 and 102 test different items but may have identical structures. Accordingly, the structure of the testing unit 101 will be described in detail below. Also, in the microfluidic device according to the current exemplary embodiment, the two testing units 101 and 102 are configured to receive samples from one sample chamber 10. However, the present invention is not limited to this configuration, and two sample chambers that respectively supply samples to the testing units 101 and 102 may also be provided.

A sample separator 30 that centrifuges a sample using the rotation of the platform 100 is disposed in an outer portion of the sample chamber 10. The sample separator 30 may be formed in various shapes, and one example thereof is illustrated in FIG. 1. The sample separator 30 is connected to the sample chamber 10. The sample separator 30 includes a supernatant collector 311 which is a channel-shaped and extends from the sample chamber 10 to the outside, and a precipitation collector 312 that is positioned at an end of the supernatant collector 311 and provides a space for collecting precipitation having large mass. The excess amount of the sample can be accommodated in an excess sample storing unit 20 that is connected to the supernatant collector 311 via a channel 21. Although not illustrated in FIG. 1, a valve, which is also operated by electromagnetic waves, may be provided in the channel 21. A sample distribution channel 314 distributes a collected supernatant, for example, serum, in the case when blood is used as a sample, to a next structure and is disposed at a side of the supernatant collector 311. The sample distribution channel 314 is connected to the supernatant collector 311 via a valve 313. The connection position of the sample distribution channel 314 may vary according to the amount of the supernatant to be distributed. That is, the amount of the supernatant to be distributed depends on the volume of a portion of the supernatant collector 311 that is near to the center C at the side of the valve 313. In detail, as will be described later, when a measuring chamber 50 is further included, the amount of the sample to be distributed depends on the capacity of the measuring chamber 50.

The valve 313 may be a microfluidic valve that may have one of various shapes. The valve 313 may be a capillary valve which is opened passively when predetermined pressure is applied, or a valve that is actively operated by receiving motive power or energy from the outside via operational signals.

The valve 313 is a normally closed valve which closes the channel 314 so that no fluid can flow through before absorbing electromagnetic waves.

The valve 313 may be formed of a thermoplastic resin such as COC (cyclic olefin copolymer), PMMA (polymethylmethacrylate), PC (polycarbonate), PS (polystyrene), POM (polyoxymethylene), PFA (perfluoroalkoxy), PVC (polyvinylchloride), PP (polypropylene), PET (polyethylene terephthalate), PEEK (polyetheretherketone), PA (polyamide), PSU (polysulfone), or PVDF (polyvinylidene fluoride).

Also, the valve 313 may be formed of a phase change material which is solid at a room temperature. A phase change material is loaded into the channel 314 in a fused state and solidified, thereby blocking the channel 314. The phase change material may be wax. When heated, wax is fused, liquefied and expanded. Examples of the wax include paraffin wax, microcrystalline wax, synthetic wax, and natural wax, etc. The phase change material may be a gel or thermoplastic resin. Examples of the gel include polyacrylamide, polyacrylates, polymethacrylates, and polyvinylamides.

A plurality of minute heat generating particles, which absorb electromagnetic wave energy and generate heat, may be distributed in the phase change material. The minute heat generating particles have a diameter of 1 μm to 100 μm so that they can freely pass through the minute channel 314 which has a depth of approximately 0.1 mm and a width of 1 mm. When electromagnetic wave energy is supplied, the temperature of the minute heat generating particles is abruptly raised, and the heat generating particles generate heat and are uniformly distributed in the wax. The minute heat generating particles may have cores containing metal components and a hydrophobic surface structure so as to have the properties described above. For example, the minute heat generating particles may have a molecule structure including cores formed of Fe and a plurality of surfactants that are bonded to the Fe so as to surround the Fe. The minute heat generating particles may be stored by being distributed in a carrier oil. The carrier oil may preferably be hydrophobic as well, so that the minute heat generating particles having a hydrophobic surface structure can be uniformly distributed in the carrier oil. The carrier oil in which the minute heat generating particles are distributed is poured into the fused phase change material and mixed, and this mixed material is loaded into the channel 314 and solidified, thereby blocking the channel 314.

The minute heat generating particles are not limited to the polymer particles as described above, and may also be quantum dots or magnetic beads. Also, the minute heat generating particles may be minute metal oxides such as $Al_2O_3$, TiO2, $Ta_2O_3$, $Fe_2O_3$, $Fe_3O_4$ or $HfO_2$. The valve 313 need not contain minute heat generating particles necessarily but may be formed of a phase change material only. At least a portion of the platform 100 is transparent so that electromagnetic waves projected from the outside of the platform 100 can be irradiated to the valve 313.

The measuring chamber 50 is connected to the channel 314 and receives and accommodates the supernatant separated from the sample by the sample separator 30. The measuring chamber 50 is also connected to a dilution chamber 60 via a valve 51. The valve 51 may be a microfluidic valve of the same structure as that of the valve 313 described above.

The dilution chamber 60 is for providing a sample diluent in which a supernatant and a diluent are mixed at a predetermined ratio. A predetermined amount of dilution buffer is accommodated in the dilution chamber 60 in consideration of the dilution ratio of the supernatant to the diluent, which is required for the test. The measuring chamber 50 is designed to have a capacity capable of accommodating a predetermined amount of the sample in consideration of the dilution ratio. As long as the valve 51 remains in the closed state, a sample exceeding the capacity of the measuring chamber 50 cannot be loaded into the measuring chamber 50. Accordingly, only a fixed amount of the sample can be supplied to the dilution chamber 60.

Alternatively, by precisely designing the connection position of the channel 314 and the supernatant collector 311, the channel 314 and the dilution chamber 60 may be directly connected to each other without the measuring chamber 50 being interposed between the channel 314 and the dilution chamber 60.

A plurality of reaction chambers 70 are disposed exterior to the dilution chamber 60. The reaction chambers 70 are connected to the dilution chamber 60 via a distribution channel 61. Distribution of the sample diluent through the distribution channel 61 may be controlled by a valve 62. The valve 62 may be a microfluidic valve having the same shape as that of the above-described valve 313.

In the reaction chambers 70, reagents that react differently with the sample diluents may be accommodated. The reagents may be loaded during the manufacture of the microfluidic device before bonding the upper layer 12 and the lower layer 11 to form the platform 100. Also, instead of a closed type reaction chamber, the reaction chambers 70 may be any reaction chamber that has a vent and a loading opening. In the case of such a reaction chamber, the reagents may be loaded into the reaction chambers 70 prior to conducting the tests. The reagents may be liquid or in a lyophilized solid state. For example, a liquid reagent may be loaded into the reaction chambers 70 before bonding the upper and lower layers 12 and 11 to form the platform 100 during the manufacture of the microfluidic device, and may be lyophilized at the same time by a lyophilization program. Then, by bonding the upper and lower layers 12 and 11, a microfluidic device containing the lyophilized reagent is provided. Also, a cartridge in which the lyophilized reagent is accommodated may be loaded into the reaction chambers 70. The lyophilized sample may be provided by adding a filler and a surfactant to a liquid reagent and lyophilizing the mixture. The filler ensures the lyophilized reagent has a porous structure so that the sample diluent in which the sample and the diluent are mixed can be easily dissolved when the sample diluent is loaded into the reaction chambers 70 later. For example, the filler may be one of BSA (bovine serum albumin), PEG (polyethylene glycol), dextran, mannitol, polyalcohol, myo-inositol, citric acid, EDTA2Na (ethylene diamine tetra acetic acid disodium salt), and BRIJ-35 (polyoxyethylene glycol dodecyl ether). According to the type of the reagent, at least one or two fillers may be selected and added. For example, the surfactant may be one of polyoxyethylene, lauryl ether, octoxynol, polyethylene alkyl alcohol, nonylphenol polyethylene glycol ether; ethylene oxide, ethoxylated tridecyl alcohol, polyoxyethylene nonylphenyl ether phosphate sodium salt, and sodium dodecyl sulfate. According to the type of the reagent, at least one or two surfactants may be selected and added.

The microfluidic device according to the current exemplary embodiment further includes first and second concentration detecting chambers 40 and 80. The first and second concentration detecting chambers 40 and 80 are provided for checking whether the dilution ratio of the sample diluent is appropriate for the test. The sample is accommodated in the first concentration detecting chamber 40. If a sample does not require centrifuging, the sample may be directly supplied from the sample chamber 10 to the first concentration detecting chamber 40. Since the microfluidic device according to the current exemplary embodiment includes a sample separator 30, a supernatant that is separated from the sample is accommodated in the first concentration detecting chamber 40. The first concentration detecting chamber 40 is connected to the channel 314. When the channel 314 is opened by the valve 313, the supernatant flows into the first concentration detecting chamber 40. The second concentration detecting chamber 80 accommodates a sample diluent. For example, the second concentration detecting chamber 80 is connected to the dilution chamber 60 via the distribution channel 61. When the valve 62 is opened, the sample diluent flows through the distribution channel 61 into the second concentration detecting chamber 80. The first and second concentration detecting chambers 40 and 80 may preferably, but not necessarily, be positioned at the same distance from the rotational center C of the platform 100. Also, distances from the rotational center C to the first and second concentration detecting chambers 40 and 80 may preferably, but not necessarily, the same as distances from the rotation center C to the reaction chambers 70. In an analyzing process which will be described later, a detector 520 of FIG. 4 and the first and second concentration detecting chambers 40 and 80 can be made to face each other, for the sake of convenience, not by moving the detector 520 but instead by simply rotating the microfluidic device. The microfluidic device according to the current exemplary embodiment includes one first concentration detecting chamber 40 and one second concentration detecting chamber 80; however, two or more of each of the first and second concentration detecting chambers 40 and 80 may also be included in the microfluidic device.

A reference unit 103, which does not receive a sample from the sample chamber 10, may be formed in the platform 100. The reference unit 103 may include a dilution chamber 610 and a plurality of chambers 620 connected to the dilution chamber 610. A diluent may be stored in the dilution chamber 610 to obtain standard values when detecting reactions. The chambers 620, which are empty or filled with distilled water may be disposed exterior to the dilution chamber 610 to obtain detection standard values.

Although not shown, an air vent for discharging air in the microfluidic device and a loading opening for loading materials for the test may be provided in the microfluidic device.

Figure 4:
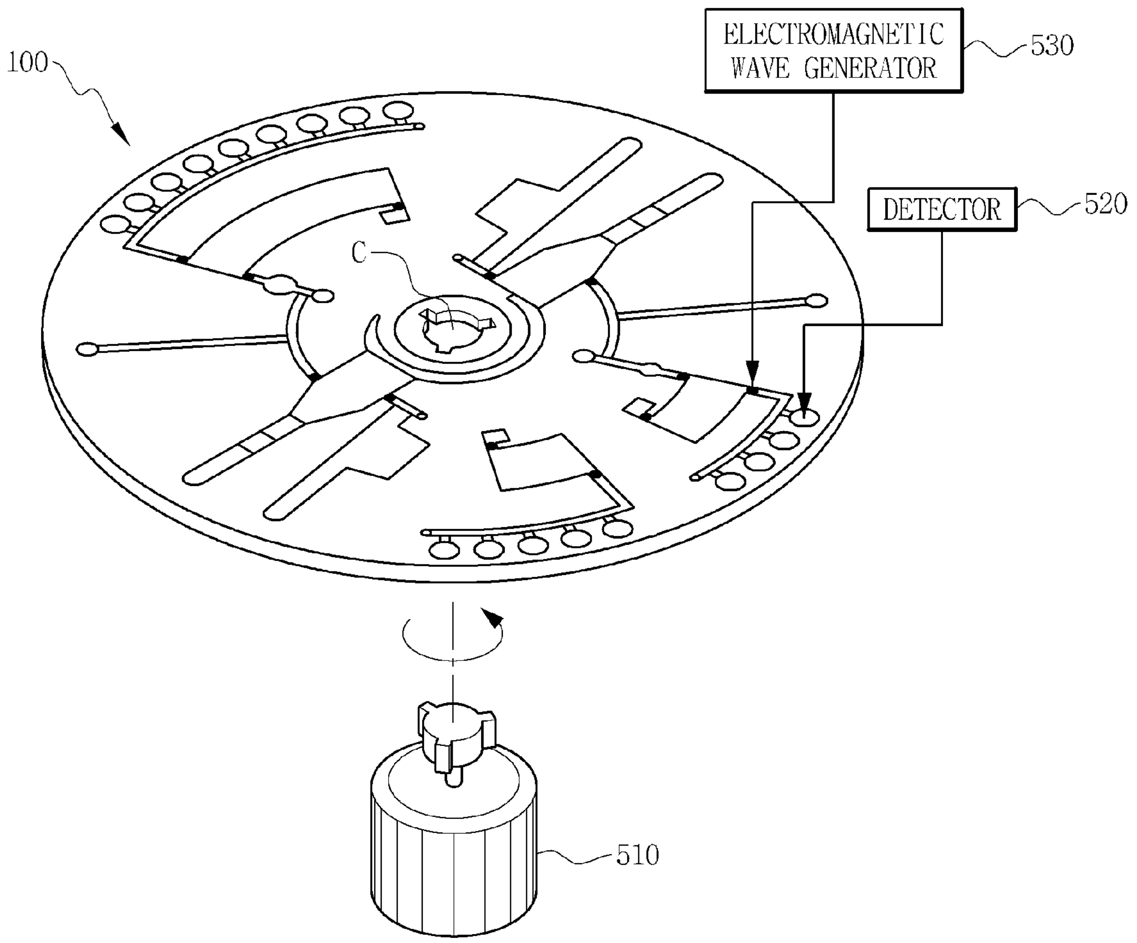
FIG. 4 is a schematic view of an analyzer including the microfluidic device of FIG. 1.

FIG. 4 shows a schematic view of an analyzer including the microfluidic device of FIG. 1. Referring to FIG. 4, a rotational driving unit 510 rotates the microfluidic device in order to centrifugally separate a sample and to move a separated supernatant to a predetermined position in the microfluidic device. Also, the rotational driving unit 510 stops the microfluidic device at a predetermined position in which that the reaction chamber 70 and the detector 520 face each other. Although the rotational driving unit 510 is only partially illustrated in FIG. 4, the rotational driving unit 510 may further comprise a motor driving unit which can control the angular position of the microfluidic device. For example, the motor driving unit may use a step motor or a direct current motor. The detector 520 detects optical characteristics such as fluorescent, luminescent, and/or absorbent characteristics, of a material to be detected. An electromagnetic wave generator 530 irradiates, for example, laser light to operate the valves 62 and 313. The electromagnetic wave generator 530 may be moved in radial directions of the microfluidic device.

Hereinafter, a sample analyzing process using the above-described microfluidic device will be described. In the current exemplary embodiment, a process of analyzing blood will be described.

Blood collected from an examinee is loaded into the sample chamber 10. A liquid diluent such as buffer solution or distilled water is loaded into the dilution chamber 60. Here, a predetermined amount of the diluent is loaded into the dilution chamber 60 so that the dilution ratio of the sample diluent is appropriate for a certain test item. For example, the microfluidic device according to the current exemplary embodiment includes two testing units 101 and 102, which are connected to the sample chamber 10. For example, in the case of the testing unit 101, if the capacity of the measuring chamber 50 is 17 uL, a diluent of 1700 uL is accommodated in the dilution chamber 60 to match the dilution ratio of 1:100. Also, if the capacity of the measuring chamber 50 of the testing unit 102 is 45 uL, a diluent of 900 uL is accommodated in the dilution chamber 60 to match the dilution ratio of 1:20.

The microfluidic device is mounted in the rotational driving unit 510 of the analyzer as illustrated in FIG. 4. The rotational driving unit 510 rotates the microfluidic device. Then the sample accommodated in the sample chamber 10 is moved by centrifugal force to the sample separator 30. An excess amount of the sample is moved to the excess sample storing unit 20 through the channel 21. As the microfluidic device is rotated further, only a supernatant is collected in the supernatant collector 311, and materials having a large mass are collected in the precipitation collector 312.

The rotational driving unit 510 makes the valve 313 face the electromagnetic wave generator 530. When an electromagnetic wave is irradiated to the valve 313, the material forming the valve 313 is fused by the electromagnetic wave energy, and the channel 314 is opened. As the microfluidic device is rotated, the supernatant is moved by centrifugal force to the measuring chamber 50 and to the first concentration detecting chamber 40 along the channel 314.

The rotational driving unit 510 makes the valve 51 face the electromagnetic wave generator 530. When an electromagnetic wave is irradiated to the valve 51, the material forming the valve 51 is fused by the electromagnetic wave energy, and the supernatant is loaded to the dilution chamber 60. The rotational driving unit 510 may shake the microfluidic device to the left and right several times in order to mix the supernatant and the diluent. Accordingly, a sample diluent in which the supernatant and the diluent are mixed is generated in the dilution chamber 60.

The rotational driving unit 510 makes the valve 62 face the electromagnetic wave generator 530. When an electromagnetic wave is irradiated to the valve 62, the material forming the valve 313 is fused by the electromagnetic wave energy, and a distribution channel 61 is opened. As the microfluidic device is rotated, the sample diluent is loaded by centrifugal force to the reaction chambers 70 and the second concentration detecting chamber 80 through the distribution channel 61. A reagent accommodated in the reaction chambers 70 are mixed with the sample diluent. The rotational driving unit 510 may shake the microfluidic device to the left and right several times in order to mix the sample reagent and the sample diluent.

Next, the reaction chambers 70 are made to sequentially face the detector 520, and light is irradiated to the mixture of the reagent and the sample diluent in the reaction chambers 70 to detect optical characteristics such as fluorescent, luminescent, and/or absorbent characteristics of the mixture. Thus, whether a predetermined material is present in the mixture and the amount of the material can be detected.

In order to check the reliability of the sample analysis, the dilution ratio of the sample diluent is measured. To this end, the rotational driving unit 510 makes the first and second concentration detecting chambers 40 and 80 sequentially face the detector 520 and measures light absorption values of the sample in the first concentration detecting chamber 40 and the sample diluent in the second concentration detecting chamber 80.

The dilution ratio of the sample diluent greatly influences the accuracy of detection. For example, if a detection signal is too weak or too strong, the detection range can be adjusted by controlling the dilution ratio, and the dilution ratio is determined so as to obtain an optimum test result according to the test items. Accordingly, if the dilution ratio of the sample diluent is an optimum dilution ratio that is determined in advance, the test result is deemed to be reliable. If the dilution ratio of the sample diluent is not an optimum dilution ratio, the test result is deemed to be unreliable.

According to the Beer-Lambert Law, the light absorption is in proportion to the concentration of the sample and the length of an optical path. That is, when the concentration of the sample remains constant and lengths of the optical path differ, the light absorption value of the sample varies in proportion to the lengths of the optical path. Also, when the length of the optical path remains constant and concentrations of the sample differ, the light absorption value of the sample varies in proportion to the concentrations of the sample. Accordingly, even when the concentration of the sample before being diluted is not known, the light absorption of the sample diluent can be estimated by measuring the light absorption of the sample.

When a sample having a concentration C is put into a chamber having a depth L1, a light absorption value of the sample is A1; when the same sample having the concentration C is put into a chamber having a depth L2, the light absorption value of the sample is A2=(L2/L1)A1. For example, when L1 is 6 mm and L2 is 1.2 mm, A2 is (1/5)A1. Also, when L1 is 6 mm and L2 is 0.6 mm, A2 is (1/10)A1.

Then, by using the sample having the concentration C, a sample diluent having a 1:B dilution ratio of the sample to the diluent is prepared. The sample diluent is then accommodated in a chamber having a depth L3, and a light absorption value of the sample diluent here is referred to as A3. The concentration of the sample in the sample diluent is C/B, and since the light absorption value is in proportion to the length of the optical path, A3 is (1/B)(L3/L1)A1. For example, when L1=L3=6 mm and B=100, A3 is (1/100)A1. Also, when L1=6 mm, L3=1.2 mm, and B=100, A3 is (1/20)A1. Also, when L1=6 mm, L3=1.2 mm, and B=20, A3 is (1/20)(1/5)A1=(1/100) A1.

While the depths of the first and second concentration detecting chambers 40 and 80 are determined during the manufacture of the microfluidic device and thus are known already, the light absorption value of the sample diluent having a predetermined dilution ratio can be estimated by measuring the light absorption value of the supernatant in the first concentration detecting chamber 40. Accordingly, when the light absorption value of the sample diluent measured in the second concentration detecting chamber 80 is the same as or within the allowable error range of the light absorption value of the sample diluent estimated from the light absorption value of the supernatant measured in the first concentration detecting chamber 40, the dilution ratio of the sample diluent can be judged as being appropriate, and the result of the test can also be reliable. Also, the dilution ratio of the sample diluent can be calculated from the light absorption value of the sample diluent measured in the second concentration detecting chamber 80 and the light absorption value measured of the supernatant in the first concentration detecting chamber 40, and when the calculated dilution ratio of the sample diluent is to the same as or within the allowable error range of a desired dilution ratio, the test result can be reliable. According to the above-described method, the dilution ratio of the sample diluent can be measured from the light absorption values and the lengths of the optical paths even when the concentration of the sample (supernatant) is not known, and the reliability of the test can be proved.

In the current exemplary embodiment, the reliability of the test is checked using one first concentrations detecting chamber 40 and one second concentration detecting chamber 80. However, the present invention is not limited thereto. For example, to one of ordinary skill in the art, it may be known that when two or more first concentration detecting chambers 40 are included, the dilution ratio of the sample diluent can be estimated by using the average light absorption value of the first concentration detecting chambers or by calculating a relationship between the concentration of the sample and light absorption values of the sample diluent as an equation, and using this equation. Also, it may be known to one of ordinary skill in the art that two or more second concentration detecting chambers 80 can be included.

In the above-described description, a sample and a supernatant are used together. However, the sample separator 30 may be omitted when centrifuged serum is loaded into the sample chamber 10, and in this case, the term 'supernatant' is not necessary. Accordingly, it may be known to one of ordinary skill in the art that the sample and the supernatant in the above-described description mean serum. Also, it may be known to one or ordinary skill in the art that the sample that has passed through the sample separator 30 means a supernatant in the case when blood is loaded into the sample chamber 10.

Also, in the above-described description, blood has been analyzed as an example. However, the present invention is not limited thereto. The microfluidic device according to the current exemplary embodiment may also be used to analyze various kinds of extracted material that can be extracted from the human body or other animate objects, and also various other materials extracted from nature, other than blood.

While aspects of the inventive concept have been particularly shown and described with reference to differing exemplary embodiments thereof, it should be understood that these exemplary embodiments should be considered in a descriptive sense only and not for purposes of limitation. Descriptions of features or aspects within each exemplary embodiment should typically be considered as available for other similar features or aspects in the remaining exemplary embodiments.

Thus, although a few exemplary embodiments have been shown and described, it would be appreciated by those of ordinary skill in the art that changes may be made in these exemplary embodiments without departing from the principles and spirit of the invention, the scope of which is defined in the claims and their equivalents.

What is claimed is:

1. A microfluidic device comprising:

a sample chamber which accommodates a sample to be tested;

a dilution chamber which accommodates a diluent and is connected with the sample chamber by a sample distribution channel, wherein the dilution chamber receives the sample from the sample chamber and provides a sample diluent;

a first concentration detecting chamber which extends from the sample distribution channel and is disposed between the sample chamber and the dilution chamber, and which receives the sample from the sample chamber;

a plurality of reaction chambers which accommodate a reagent and receive a portion of the sample diluent from the dilution chamber; and a second concentration detecting chamber which is disposed between the dilution chamber and the plurality of reaction chambers, and receives the sample diluent from the dilution chamber.

2. The microfluidic device of claim 1, wherein the microfluidic device has a disk shape.

3. The microfluidic device of claim 1, further comprising a sample separator which separates the sample supplied from the sample chamber, wherein a supernatant of the separated sample is supplied from the sample separator to the dilution chamber and the first concentration detecting chamber.

4. The microfluidic device of claim 3, further comprising a measuring chamber which receives and accommodates a fixed amount of the supernatant from the sample separator, the measuring chamber being disposed between the sample separator and the dilution chamber.

5. The microfluidic device of claim 4, further comprising an excess sample storing unit that is connected to the sample separator and stores an excess amount of the sample.

6. The microfluidic device of claim 1, wherein the first and second concentration detecting chambers are positioned at a same distance from a rotation center of the microfluidic device.

7. The microfluidic device of claim 1, wherein distances from a rotation center of the microfluidic device to the first and second concentration detecting chambers are the same as distances from the rotation center of the microfluidic device to the plurality of reaction chambers.

8. The microfluidic device of claim 1, comprising a plurality of the first concentration detecting chambers.

9. The microfluidic device of claim 1, comprising a plurality of the second concentration detecting chambers.

10. The microfluidic device of claim 1, comprising a plurality of dilution chambers which provide a plurality of sample diluents having different dilution ratios.

11. A microfluidic device comprising:

a sample chamber which accommodates a sample to be tested;

a sample separator which is connected to the sample chamber, receives the sample from the sample chamber and separates a supernatant from the sample;

a sample distribution channel which is connected to the sample separator;

a dilution chamber which accommodates a diluent, receives a portion of the supernatant separated by the sample separator via the sample distribution channel, and provides a sample diluent in which the portion of the supernatant and a diluent are mixed at a predetermined ratio;

a first concentration detecting chamber which receives another portion of the supernatant separated by the sample separator via the sample distribution channel;

a measuring chamber which is disposed within the sample distribution channel between the sample separator and the dilution chamber;

a plurality of reaction chambers which accommodate a reagent and receive another portion of the sample diluent from the dilution chamber; and a second concentration detecting chamber which is disposed between the dilution chamber and the plurality of reaction chambers and receives a portion of the sample diluent from the dilution chamber.

12. The microfluidic device of claim 11, further comprising:

a first valve interposed between the sample distribution channel and the sample separator; and a second valve interposed between the dilution chamber and the second concentration chamber and the at least one reaction chamber, wherein the first and second valves are formed of a phase change material which melts when irradiated with electromagnetic energy so the first and second valves are opened.

* * * * *